United States Patent [19]

Holm et al.

[11] Patent Number: 4,973,318
[45] Date of Patent: Nov. 27, 1990

[54] DISPOSABLE SYRINGE

[75] Inventors: Niels E. Holm, Birkerod; Allan Spork, Lyngby; Klaus Thogersen, Klampenborg; Anders Bressendorff, Virum; Jorn Rex, Roskilde, all of Denmark

[73] Assignee: D.C.P. AF 1988 A/S, Denmark

[21] Appl. No.: 308,399

[22] Filed: Feb. 9, 1989

[30] Foreign Application Priority Data

Feb. 10, 1988 [DK] Denmark ............................... 692/88

[51] Int. Cl.$^5$ ................................................ A61M 5/00
[52] U.S. Cl. ..................................... 604/208; 604/211; 604/218
[58] Field of Search ............... 604/206, 207, 208, 209, 604/210, 211, 187, 232, 236, 246, 248, 192, 263, 71, 72, 186, 218

[56] References Cited

U.S. PATENT DOCUMENTS

| | | |
|---|---|---|
| 1,997,129 | 4/1935 | Taylor et al. . |
| 2,605,763 | 8/1952 | Smoot . |
| 2,695,023 | 11/1954 | Brown . |
| 2,718,299 | 9/1955 | Atwater et al. . |
| 2,826,195 | 3/1958 | Ashkenaz . |
| 3,138,157 | 6/1964 | Ziherl et al. ........................ 604/71 |
| 3,348,545 | 10/1967 | Sarnoff et al. . |
| 3,517,668 | 6/1970 | Brickson . |
| 3,790,048 | 2/1974 | Luciano et al. . |
| 3,894,663 | 7/1975 | Carhart et al. . |
| 3,905,366 | 9/1975 | Callahan et al. . |
| 3,977,574 | 8/1976 | Thomas . |
| 4,022,207 | 5/1977 | Citrin . |
| 4,099,548 | 7/1978 | Sturm et al. . |
| 4,103,684 | 8/1978 | Ismach ................................. 604/71 |
| 4,244,366 | 1/1981 | Raines . |
| 4,246,898 | 1/1981 | Travalent et al. . |
| 4,275,729 | 6/1981 | Silver et al. . |
| 4,395,921 | 8/1983 | Oppenlander . |
| 4,413,760 | 11/1983 | Paton . |
| 4,415,101 | 11/1988 | Shapiro et al. . |
| 4,457,712 | 7/1984 | Dragan . |
| 4,470,317 | 9/1984 | Sabloewaki et al. . |
| 4,475,905 | 10/1984 | Himmelstrup . |
| 4,498,904 | 2/1985 | Turner et al. . |
| 4,583,973 | 4/1986 | Humphrey et al. ................. 604/218 |
| 4,583,978 | 4/1986 | Porat et al. . |
| 4,592,745 | 6/1986 | Rex et al. . |

FOREIGN PATENT DOCUMENTS

| | | |
|---|---|---|
| 0037696 | 4/1960 | European Pat. Off. . |
| 0064858 | 5/1981 | European Pat. Off. . |
| 0143895 | 8/1984 | European Pat. Off. . |
| 0226718 | 12/1985 | European Pat. Off. . |
| 730971 | 1/1943 | Fed. Rep. of Germany . |
| 1149735 | 12/1957 | France . |
| 1170312 | 1/1959 | France . |
| 1445659 | 6/1966 | France . |
| CH84/00167 | 6/1985 | PCT Int'l Appl. . |
| CH86/00151 | 5/1987 | PCT Int'l Appl. . |
| WO88/07874 | 10/1988 | PCT Int'l Appl. . |
| 293302 | 12/1953 | Switzerland . |
| 991766 | 5/1965 | United Kingdom . |
| 1145483 | 3/1969 | United Kingdom . |
| 1225495 | 3/1971 | United Kingdom . |
| 2109690 | 2/1982 | United Kingdom . |

Primary Examiner—John D. Yasko
Attorney, Agent, or Firm—Willian Brinks Olds Hofer Gilson & Lione

[57] ABSTRACT

A disposable syringe includes first and second housing elements which are coupled together for rotation without axial movement therebetween. The first housing element receives a cartridge of a solution to be injected, and mounts a liquid outlet needle at its front end. A piston rod is disposed in the second housing element to move axially therein, and this piston rod includes a rod element and a nut element. The rod element is coupled to the first housing element to move axially therein without relative rotation therewith, and the nut element is threaded to the rod element for telescoping movement therewith and is configured to move axially in the second housing element without relative rotation therein. A pressure receiving element is mounted on the nut element. The housing, rod, nut and pressure receiving elements cooperate such that relative rotation between the housing elements in a selected direction causes relative rotation between the nut and rod elements and thereby increases the effective length of the piston rod and causes the pressure receiving element to extend from the second housing element. A protective cap is removably mounted over the first housing element and is configured to abut second housing element while mounted in place on the first housing element. This protective cap is engaged with the first housing element such that rotation of the cap with respect to the second housing element causes rotation of the first housing element with respect to the second housing element.

30 Claims, 9 Drawing Sheets

DISPOSABLE SYRINGE

TECHNICAL FIELD

This invention relates to a disposable syringe for injecting preset doses of a liquid contained in the syringe. The syringe of this invention is particularly but not exclusively applicable for delivering preset dosages of insulin, and the following description relates to a device for the injection of insulin solutions. However, it is to be understood that the syringe of this invention is also suitable for the injection of preset dosages of other liquids.

In particular, this invention relates to a syringe or dosage unit of the type that comprises first and second housing elements coupled together to allow rotation of the first housing element with respect to the second housing element, wherein the first housing element is adapted to receive a quantity of liquid and comprises means for mounting a liquid outlet needle in the front end thereof, and wherein the second housing element has a rear end situated opposite the front end of the first housing element.

BACKGROUND ART

Diabetics have to inject themselves repeatedly with insulin solution, and the volume of insulin solution to be injected may vary from injection to injection. For this reason, diabetics need syringes which allow them to inject successive measured dosages of the same or different preset volumes of insulin solution.

A wide variety of syringes have been proposed. For example, International Patent publication No. WO 82/02662 discloses a dose metering device for use with a syringe. The metering device utilizes a manually rotatable cap which axially moves the piston in the syringe. The volume delivered by the syringe is determined by the angular stroke of the cap. This device is not fully satisfactory for use by diabetics, because it requires two hands to hold the syringe and rotate the cap. For this reason, a diabetic cannot use this device to inject insulin into a skin fold, as recommended by many physicians.

Another drawback of the above-mentioned dose metering device is that production costs are so high that in practice it must be re-used. This necessitates replacement of the syringe or at least a cartridge with a new one. During the reloading operation, dust or other contaminants may be introduced into the metering device and this may adversely affect the operation of the metering device. Furthermore, there are more and more different commercially available insulin preparations, and therefore there is an increasing risk that a patient may insert a syringe or cartridge containing an insulin preparation other than the required one. Furthermore, reloading requires a series of operations which although not complicated may yet be troublesome for the patient.

It is therefore an object of this invention to provide a syringe that is so simple and inexpensive that it can be discarded after use.

Another object of this invention is to provide a syringe capable of delivering a number of accurate preset doses without reloading.

A further object of the invention is to provide a syringe which can be used for a single handed operation, with preadjustment of the total quantity to be injected.

A further object of the invention is to provide a syringe of such dimensions that it can be carried in a pocket like a writing pen.

Yet another object of this invention is to provide a dosage unit that maintains a constant length in use.

SUMMARY OF THE INVENTION

According to a first aspect of this invention, a disposable syringe of the type described above comprises a piston rod disposed in the second housing element to move axially therein. This piston rod comprises a rod element and a nut element. The rod element is coupled to the first housing element to move axially therein without relative rotation therebetween; and the nut element is threaded to the rod element for telescoping movement therewith and is configured to move axially in the second housing element without relative rotation therebetween. A pressure receiving element is mounted on the nut element, and the housing, rod, nut and pressure receiving elements all cooperate such that relative rotation between the housing elements in a selected direction causes relative rotation between the rod and nut elements and thereby increases the effective length of the piston rod and causes the pressure receiving element to extend from the second housing element. In this way, a measured quantity of the liquid is expressed from the needle when the pressure receiving element is moved back toward the second housing element.

Preferably, the nut element defines an axial scale along its length and is used in combination with the second housing element to gauge the dosage of liquid to be administered. As described below, the first and second housing elements may be arranged to rotate with respect to one another without axial movement therebetween such that the first and second housing elements maintain a substantially constant overall length as liquid is progressively dispensed through the needle.

The disposable syringe described below is easily preadjusted to the desired dose and quantity by rotating the two housing elements with respect to one another. This causes the nut element to move along the rod element and the pressure receiving element to be axially displaced. The indicator or scale connected to the nut element thereby moves with respect to the second housing element, and the scale can be used to measure the quantity of liquid that will be dispensed when the pressure receiving element is pushed back toward the second housing element. When the pressure receiving element is pushed back to its initial position, the nut element engages the rod element and the rod element is prevented from rotating relative to the first housing element. For this reason, axial movement of the nut element results in movement of the rod element. Preferably, a ratchet device is installed between the first housing element and the rod element to insure that the rod element cannot be retracted once it is pushed into the first housing element.

The following detailed description describes a number of other advantageous features of the invention. For example, the nut element preferably comprises at least one radially protruding, axially extending projection on the outside of the nut element which slides in an associated axially extending groove of the inner surface of the second housing element. Preferably, the nut element is shaped to limit axial movement of the nut element out of the second housing element beyond the predetermined limit, and in this way to prevent the dosage unit from being adjusted to deliver a potentially dangerously high dose of liquid. In the preferred embodiment described below, the nut element and the indicator on the nut element are integrally formed together, thereby minimizing the total number of parts and the cost of the system. In this embodiment the nut element is substantially axially symmetrically shaped, and the pressure receiving element at the external end of the nut element has an outer diameter that corresponds to the outer diameter of the second housing element. As a result, the axial movement of the nut element towards the distal or rear end of the second housing element is stopped in a simple manner.

This embodiment utilizes a rod element that is prevented from rotating relative to the first housing element by means of a ratchet device. As discussed below, at least one and preferably two pawls are provided on the first housing element, and these pawls engage longitudinal grooves in the rod element, which are provided with a suitable toothed configuration to cooperate with the pawls.

According to a second feature of this invention, a disposable syringe or dosage unit, which may, for example, be of the type described above, includes a protective cap that is removably mounted over the front end of the first housing element to protect the needle. Means are provided for releasably coupling the protective cap and the first housing element for rotation together such that rotation of the protective cap with respect to the second housing element causes rotation of the first housing element with respect to the second housing element.

Preferably, the protective cap is configured to receive the first housing element such that a front portion of the second housing element substantially abuts a rear portion of the protective cap when the protective cap is mounted in place on the first housing element. In the preferred embodiment described below, the abutting ends of the cap and the second housing element together comprise a scale for measuring relative rotation of the protective cap with respect to the second housing element. This scale allows the rotational position of the cap with respect to the second housing element, and therefore the dose to be injected, to be gauged precisely. The scale formed at the abutting ends of the cap and the second housing element indicates the rotational position of the cap in fractions of a full rotation, while the measuring scale associated with the nut element described above indicates the number of full rotations of the cap with respect to the second housing element.

In the preferred embodiment described below, the cap may be releasably engaged with the first housing element at any one of a number discrete rotational positions, and a plurality of detents are provided at corresponding increments of rotation of the first housing element with respect to the second housing element. With this arrangement it is always possible to situate the measuring scale portion of the cap opposite a fixed zero on the second housing element such that this zero position forms the basis for measuring rotation of the cap with respect to the second housing element. This is possible regardless of the detent position of the first housing element with respect to the second element, and it provides the important advantage that the user of the syringe is provided with a clear zero position at the start of each adjustment. This feature instills confidence in the user that the desired dosage has in fact been selected.

The invention itself, together with further objects and attendant advantages, will best be understood by reference to the following detailed description, taken in conjunction with the accompanying drawings.

DETAILED DESCRIPTION OF THE PREFERRED EMBODIMENTS

FIGS. 1-7, 8-18 and 19-27 relate to first, second, and third embodiments of this invention, respectively. The first and second embodiments embody both aspects of the invention described above, while the third embodiment embodies only the second aspect of the invention.

Figure 1:
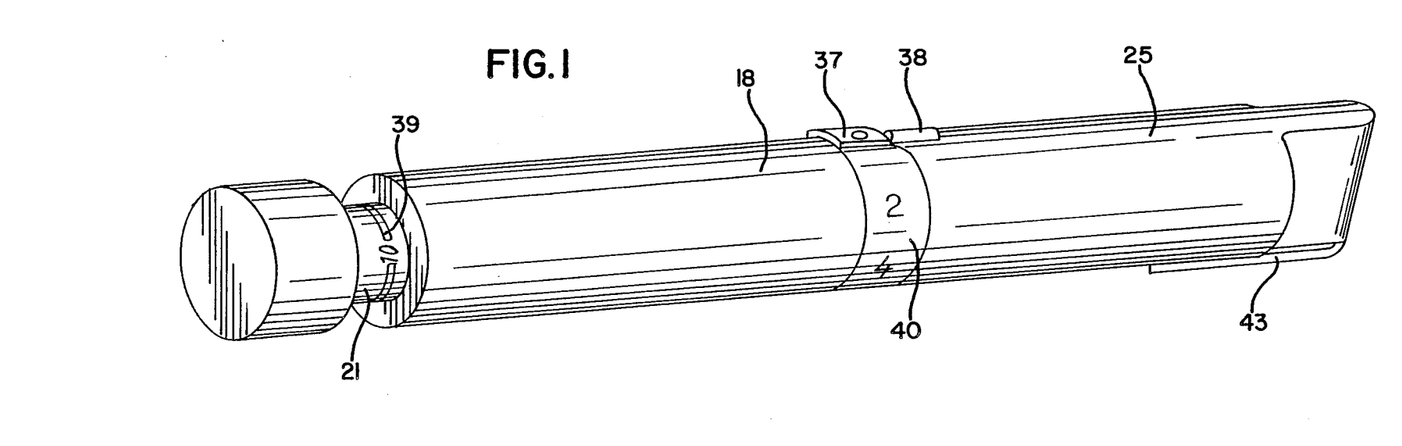
FIG. 1 is a perspective view of a first preferred embodiment of a dosage unit according to the invention, said dosage unit being ready for injection of a predetermined quantity of liquid.
Figures 2, 3:
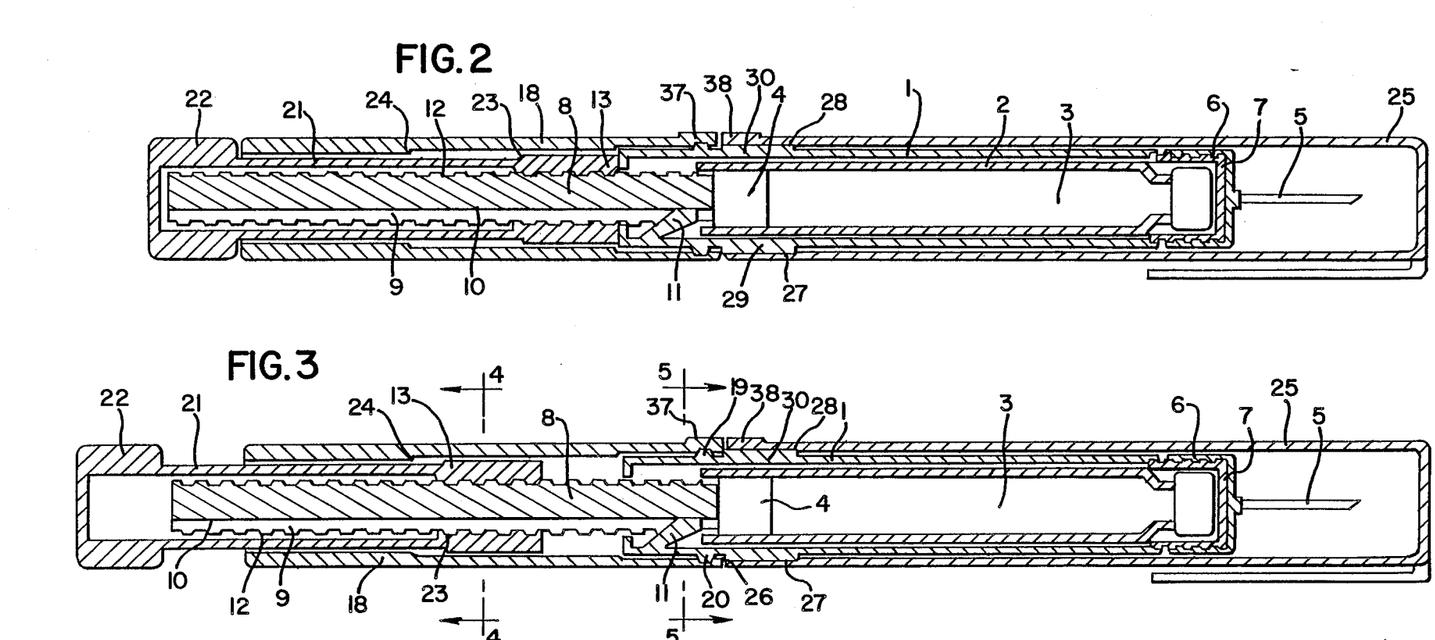
FIG. 2 is an axial sectional view of the dosage unit of FIG. 1 before the adjustment of a predetermined dosing quantity.
FIG. 3 is an axial sectional view through the dosage unit of FIG. 1.
Figure 4:
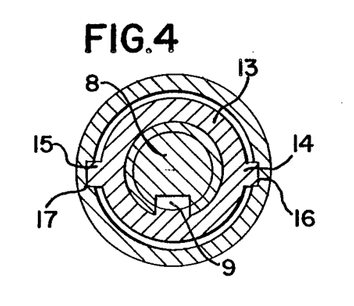
FIG. 4 is a sectional view taken along line 4—4 of FIG. 3.

Turning to FIGS. 1-7, the first embodiment comprises a first housing element or casing 1 for a cartridge 2 containing a liquid 3. The cartridge 2 comprises a piston 4 pressing the liquid 3 out through a needle 5 inserted in the opposite end, said needle being secured to the casing 1 in a generally known manner by screwing on of a cup-shaped cap 6. As indicated in FIGS. 2 and 3, the cartridge 2 can be retained in the casing by means of a retaining cap 7 optionally secured to the casing by a snapping effect. The retaining cap 7 allows introduction of a protruding end of the needle 5, said end optionally extending into the interior of the cartridge. This introduction and insertion of the needle 5 is preferably carried out during the screwing on of the needle-carrying cap 6 onto the retaining cap 7 of the casing 1.

Figure 5:
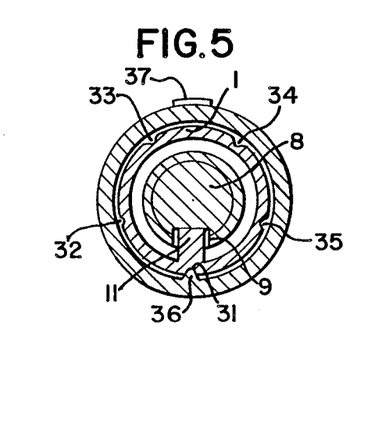
FIG. 5 is a sectional view taken along line 5—5 of FIG. 3.

At the end opposite the needle 5 the dosage unit comprises a piston rod member 8 driving the piston 4 in the cartridge 2. This piston rod member 8 comprises a longitudinal groove 9 provided in the bottom with transverse barbs 10, and the groove 9 is serrated when seen in a longitudinal section (FIG. 3). These barbs cooperate with a pawl 11 formed on the casing 1. The pawl 11 is provided with barbs which cooperate with the barbs 10 on the piston rod member 8. These barbs 10 and the pawl 11 are shaped so as only to allow displacement of the piston rod member 8 towards the piston 4 of the cartridge and to prevent displacement in the opposite direction. As indicated in FIG. 5, the pawl 11 and the groove 9 are of such a width that their cooperation prevents the piston rod member 8 from rotating relative to the casing 1.

The piston rod member 8 further comprises a thread 12 shaped along its external periphery, and a nut member 13 is screwed onto the thread 12. On the outside the nut member 13 comprises radially protruding projections 14 and 15 extending axially along the outer side of the nut member 13 and received in corresponding respective grooves 16 and 17 (FIG. 4) in a surrounding sleeve-shaped adjustment means or second housing element 18. At the end adjacent the casing 1 this adjustment means 18 comprises a circumferential groove 19 receiving a circumferential projection 20 on the casing 1. As a result the adjustment means 18 is rotatable with respect to the casing 1, yet it is prevented from moving axially.

The nut member 13 is integrally shaped with a tubular indicator 21 extending coaxially with the piston rod member 8 away from the casing 1 between the piston rod member 8 and the adjustment means 18. At the free end projecting outside the adjustment means 18, the indicator 21 comprises an end button or pressure receiving element 22 of substantially the same outer diameter as the adjustment means 18. As indicated in FIGS. 2 and 3, the nut member comprises a circumferential abutment surface 23 at the transition to the tubular indicator. Correspondingly, the adjustment means 18 comprises an inner circumferential abutment surface 24, the abutment surface 23 on the nut member abutting the abutment surface 24 to provide a predetermined stop position as the nut member is displaced in the axial direction relative to the adjustment means 18. The grooves 16 and 17 shaped on the inner side of the adjustment means 18 are of such an extent that the nut member 13 can move freely in the axial direction relative to the adjustment means between the adjacent end of the casing 1 and the inner abutment surface 24 on the adjustment means 18.

The dosage unit also includes a removable cap 25 protecting the needle 5 when the dosage unit is not used. This cap is of such an axial extent that when mounted, its free rim 26 is situated adjacent the adjustment means 18. Axial recesses or grooves are provided close to the free rim 26 of the cap 25, said recesses being situated symmetrically with the same mutual angular separation from one another along the inner side of the cap. These recesses are indicated by the reference numerals 27 and 28 in FIGS. 2 and 3 and receive correspondingly shaped protruding projections 29 and 30, respectively, on the outer side of the casing 1. In this manner the cap can always be situated in a predetermined rotational position relative to the periphery of the casing 1. Preferably the projections 29 and 30 on the casing 1 are shaped to snap into the recesses 27 and 28 on the cap 25.

As shown in FIG. 5, the casing 1 is provided with axially shaped grooves 31, 32, 33, 34 and 35 along its circumference. These grooves are situated with the same mutual angular spacing as the grooves or recesses 27 and 28 on the inner side of the cap 25. These grooves 31-35 on the outer side of the casing 1 cooperate with a projection 36 on the adjustment means 18 which projects inwardly. The grooves 31-35 and the projection 36 are shaped such that the adjustment means 18 can readily be rotated relative to the casing 1 by a user. The projection 36 cooperates with the grooves to releasably hold the casing 1 at any one of five detent positions with respect to the adjustment means, and to provide an audible click as the casing 1 is advanced from one detent position to the next.

A scale is provided on the outer side of the adjustment means 18 at the end adjacent the cap 25 (FIG. 1). This scale comprises a platform 37 with the number 0 thereon. Correspondingly, the cap 25 comprises a knob 38 to be situated opposite the platform 37. The arbitrary positioning of the cap 25 along the circumference of the casing and the corresponding positioning of the adjustment means 18 also relative to the circumference of the casing 1 renders it possible for the user always to be able to situate the knob 38 opposite the platform 37 before the adjustment is initiated.

The dosage unit of FIGS. 1-5 operates in the following manner. Upon positioning of the knob 38 opposite the platform 37 of the adjustment means 18, the desired dosing quantity is set by turning the cap 25 and therefore the casing 1 relative to the adjustment means 18. As a result, the nut member 13 is forced to follow the rotation, the abutment of said nut member 13 against the end of the casing 1 preventing a turning of the adjustment means 18 in the incorrect direction. The rotation of the nut member 13 relative to the piston rod member 8 moves the nut member 13 away from the cartridge by the thread 12, and the indicator moves axially away from the free end of the adjustment means 18. As a result, a coarse measuring scale 39 appears on the outside of the indicator 21. This scale can be configured to indicate the dosing quantity in question in full turns of the adjustment means 18 relative to the knob 38 on the cap 25, while the scale 40 on the end of the adjustment means adjacent the cap 25 indicates the dosing quantity by portions of a full rotation of the adjustment means 18 relative to the knob 38.

When the desired dosing quantity has been set, the turning of the adjustment means 18 is stopped at a suitable location defined by the inner projection 36 being received in one of the grooves 31-35 on the outside of the casing 1. Subsequently, the user removes the cap 25 and positions the dosage unit at the desired location to insert the needle 5. Then the indicator 21 is forced back into the adjustment means 18 by pressing on the end button 22 until this movement is stopped by the abutment of the nut member 13 against the end of the casing 1 or the abutment of the end button 22 against the adjacent end of the adjustment means 18. The pawl 11 prevents the piston rod member 8 from rotating, and the displacement of the indicator 21 therefore causes displacement of the piston rod member by a corresponding distance, whereby the piston of the cartridge is pressed towards the outlet end of the cartridge. As a result, a quantity of liquid is pressed out of the cartridge, said quantity corresponding to the quantity measured on the measuring scales. After completion of the injection of liquid, the dosage unit is of the same length as before the preadjustment and therefore it maintains an acceptable, uniform appearance.

A suitable choice of material allows the casing 1 to be transparent, whereby the user can always see whether liquid is left in the cartridge. The cap 25 ensures simultaneously that the contents of the cartridge are protected against sunlight. The various parts of the dosage unit are advantageously made of plastics by injection molding and are relatively easy to manufacture.

Figure 6:
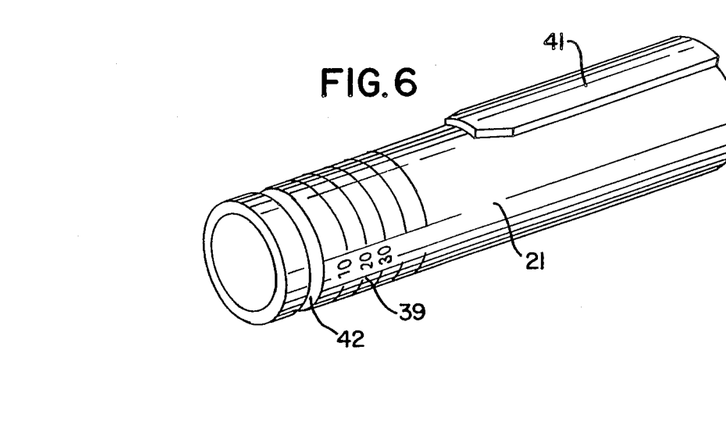
FIG. 6 is a perspective view of an embodiment of an indicator integrally formed with an associated nut member, with portions removed for the sake of clarity.
Figure 7:
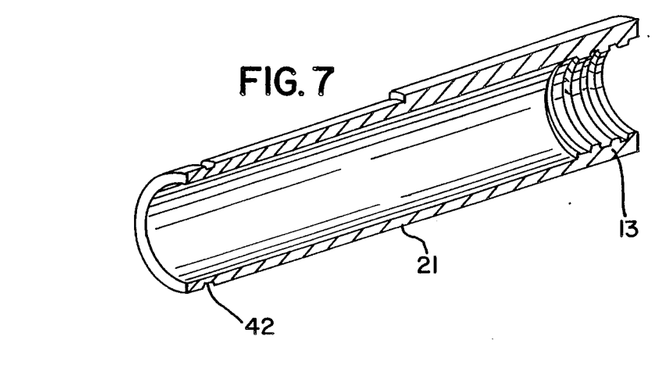
FIG. 7 is an axial sectional view of the nut member of FIG. 6.

FIGS. 6 and 7 illustrate an alternate form of the indicator 21 and the associated nut member 13. On the outside this indicator comprises a protrusion 41 received in a corresponding groove on the inside of the adjustment means 18. At the end opposite the protrusion 41, a circumferential groove 42 is provided for the fastening of a loose end knob (not shown) shaped like the end knob 22.

Many modifications can be made to the first embodiment without thereby deviating from the scope of the invention. The piston rod member may, for instance, be of different cross sections depending on the shape of the ratchet device, and the piston rod member may be prevented from rotating by a suitable shaping of the opening through which the piston rod member passes into the casing 1. Mating teeth may be provided on the end of the nut member 13 adjacent the casing 1 as well as on the abutting end of the casing 1. These teeth are preferably shaped as cooperating barbs preventing a mutual rotation of the casing 1 and the nut member towards a stronger tension. These barbs allow a slight turning in the opposite direction.

As illustrated in FIG. 1, the cap 25 is of a non-circular cross section at the end opposite the adjustment means 18 when said cap is secured on the dosage unit. In this manner it is easy to handle the cap during the mounting procedure. Furthermore, a clip 43 is provided which secures the dosage unit to a pocket in a manner similar to a fountain pen.

The second preferred embodiment of FIGS. 8-19 is similar in many respects to the first preferred embodiment described above. In view of these similarities, corresponding elements in the second embodiment are identified with the same reference numeral as in the first embodiment, with the addition of a prime. Points of similarity between the two embodiments will not be repeated, and the following discussion will focus on the differences between these embodiments.

Figure 8:
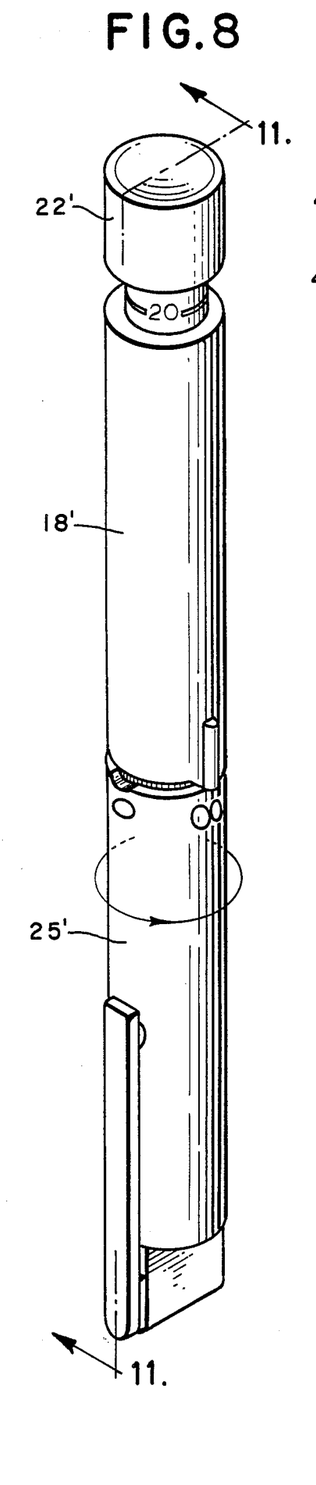
FIG. 8 is a perspective view of a second preferred embodiment of a dosage unit or disposable syringe according to this invention.
Figure 9:
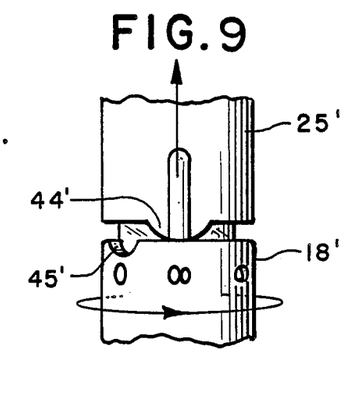
FIG. 9 is a partial view of the syringe FIG. 8, showing the cap positioned to allow rotation of the cap with respect to the second housing element of the syringe.
Figure 10:
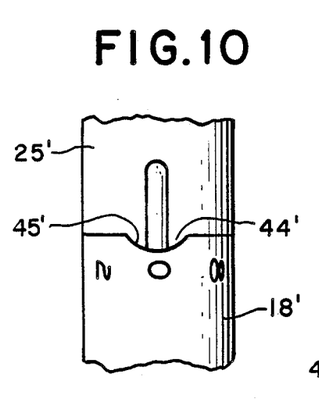
FIG. 10 is a view corresponding to FIG. 9 showing the cap seated in its zero position against the second housing element.

As best shown in FIGS. 8, 9 and 10, the illustrated disposable syringe includes a removable cap 25' which fits against the second housing element 18'. The second housing element 18' defines a projecting element 44', and the cap 25' defines a mating recess 45'. FIG. 10 shows the way in which the projecting element 44' fits within the recess 45' to define a zero position when the cap 25' is moved against the second housing element 18'. When it is desired to rotate the cap 25' with respect to the second housing element 18', the cap 25' is moved to the position shown in FIG. 9, in which the projecting element 44' is positioned outside of the recess 45', thereby allowing rotation.

Figure 11:
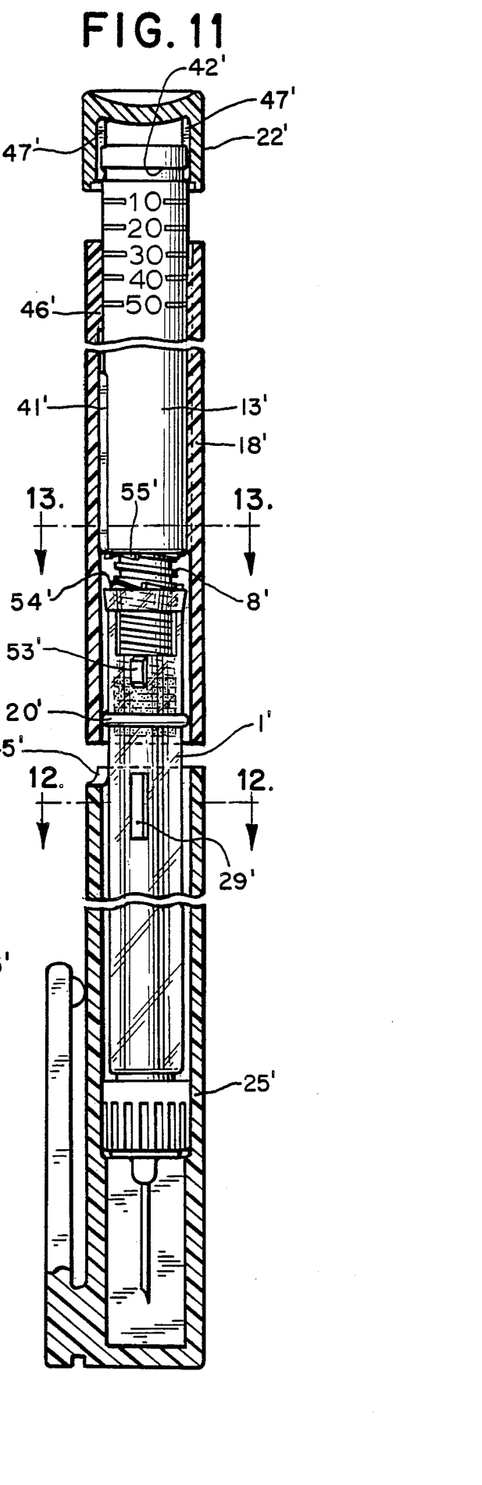
FIG. 11 is a longitudinal sectional view taken along line 11—11 of FIG. 8.
Figure 18:
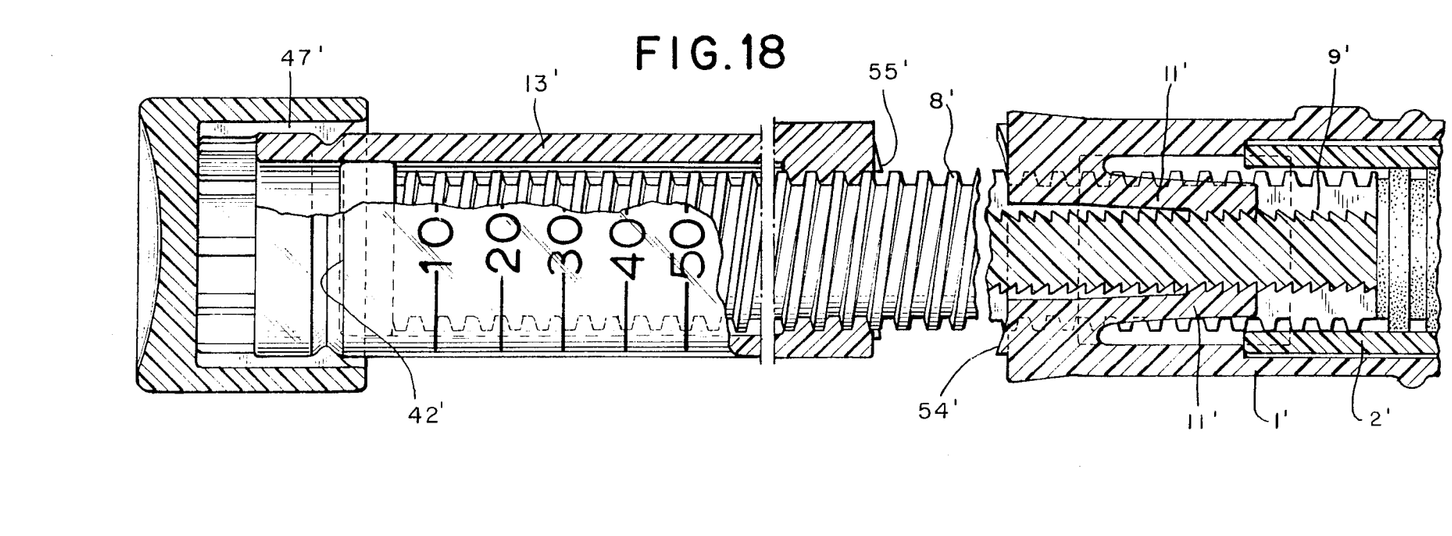
FIG. 18 is a longitudinal sectional view of components of the syringe of FIG. 8.

The nut element 13' is quite similar to that shown in FIGS. 6 and 7, and the second housing element 18' includes an internal rib 46' that cooperates with the protrusion 41' to define a stop position, beyond which the nut element 13' cannot move. The pressure receiving element 22' defines an array of internal ribs 47' on its internal surfaces, and these ribs 47' are configured to snap into and to engage the circumferential groove 42' in the nut element 13'. These ribs 47' are best shown in FIGS. 11 and 18. In this way assembly of the syringe is facilitated, without requiring adhesives of any type.

Figure 12:
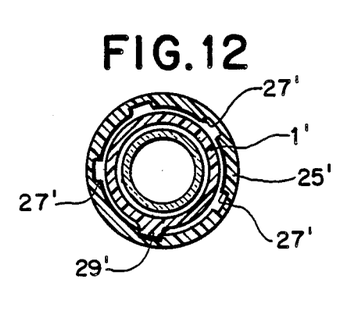
FIG. 12 is a cross-sectional view taken along line 12—12 of FIG. 11.
Figure 13:
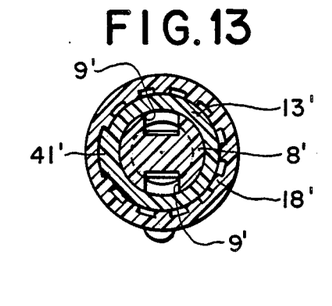
FIG. 13 is a cross-sectional view taken along line 13—13 of FIG. 11.

FIGS. 11 and 12 show the manner in which the first housing element 1' includes a projection 29' that is shaped to fit into any one of five equally spaced recesses 27' in the cap 25'.

Figures 14, 16:
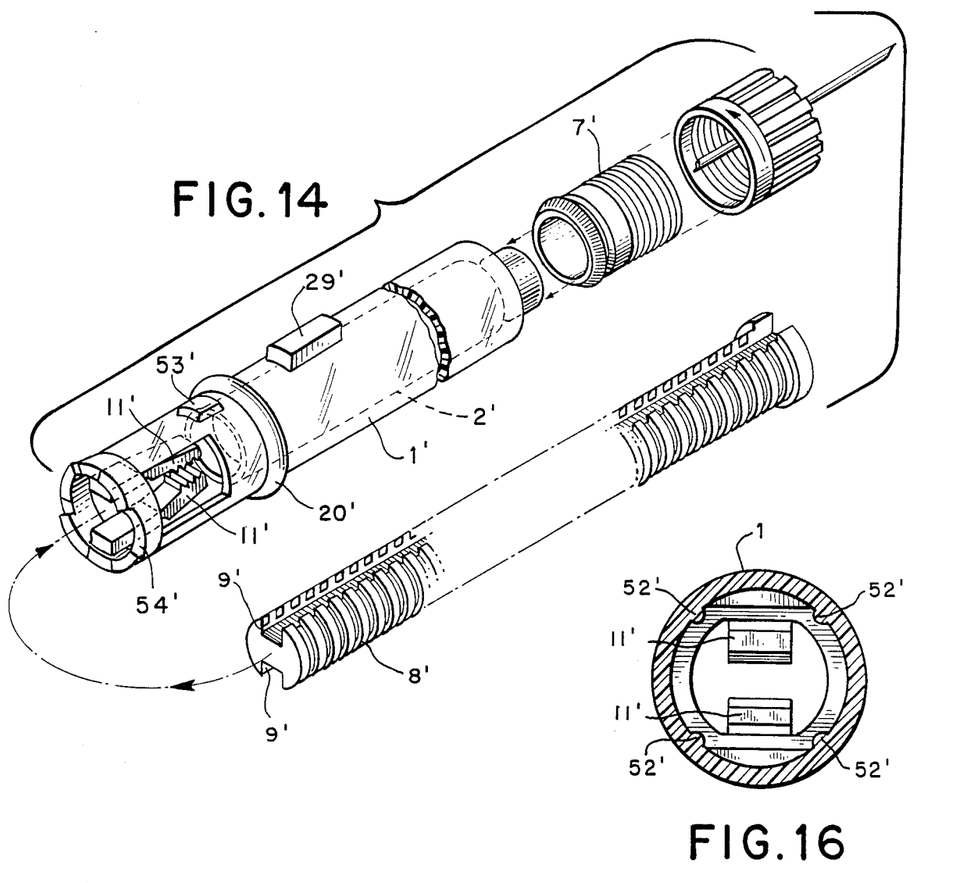
FIG. 14 is an exploded perspective view of components of the syringe of FIG. 8.
FIG. 16 is a cross-sectional view taken along line 16—16 of FIG. 15.
Figure 15:
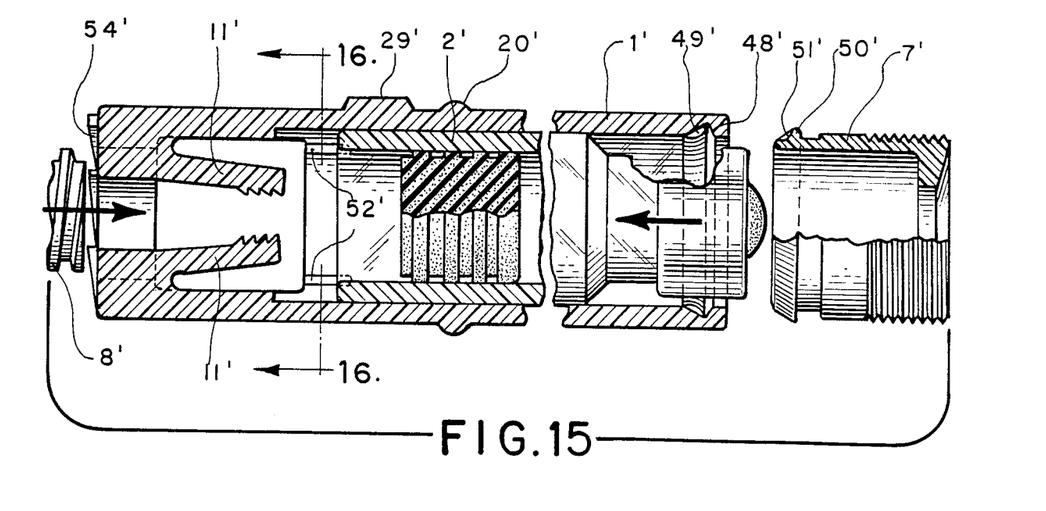
FIG. 15 is an exploded breakaway longitudinal sectional view of selected components of FIG. 14.
Figure 17:
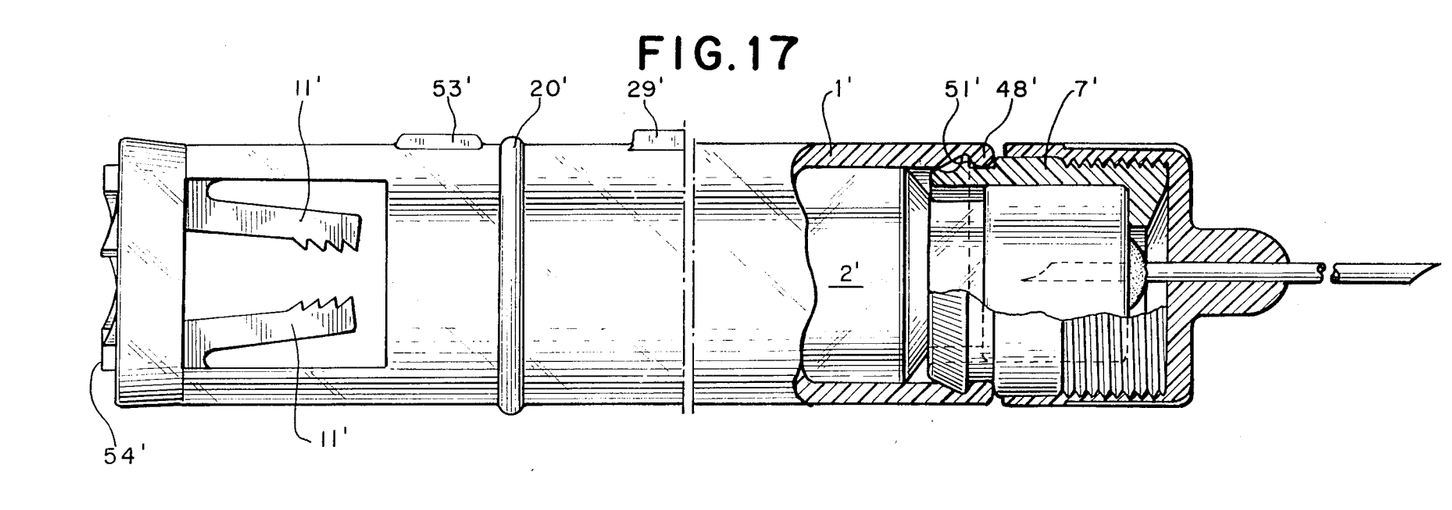
FIG. 17 is a side view in partial cut-away of selected components of FIG. 14 in the assembled position.

As best shown in FIGS. 14, 15 and 17, the first housing element 1' defines a circumferential lip 48' at its forward end, as well as a circumferential array of lugs 49'. The retaining cap 7' defines a mating groove 50', and a circumferential array of mating recesses 51'. When the retaining cap 7' is snapped in place on the first housing element 1' (FIG. 17), the lip 48' fits within the groove 50' to hold the retaining cap 7' securely in place axially. Similarly, the lugs 49' engage respective ones of the recesses 51' to prevent relative rotation between the retaining cap 7' and the first housing element 1'.

As best shown in FIGS. 14, 15 and 16, the piston rod element 8' defines two diametrically opposed longitudinal grooves 9', and the first housing element 1' includes two diametrically opposed pawls 11', each shaped to fit into a respective one of the grooves 9' to prevent relative rotation between the piston rod element 8' and the first housing element 1'. Ribs 52' (FIGS. 15 and 16) are provided to engage the cartridge 2' frictionally.

As best shown in FIGS. 11 and 14, the first housing element 1' also defines a raised lug 53' which cooperates with five equally spaced grooves in the second housing element 18' (not shown) to define five detented rotational positions of the first housing element 1' with respect to the second housing element 18'. As best shown in FIGS. 14 and 18, the first housing element 1' and the nut element 13' define respective ramps 54', 55'. These ramps are oriented to prevent relative rotation in a selected direction between the first housing element 1' and the nut element 13' when the ramps 54', 55' engage one another so as to prevent excessive stresses on the pawls 11'.

As mentioned above, the operation of the embodiment of FIGS. 8-18 is quite similar to that of the first preferred embodiment, and will not be described again here.

In the first and second embodiments described above, the piston rod is in each case a two-part assembly made up of a piston rod element and a nut element. However, this is not essential for all syringes using the protective cap of this invention, and the third preferred embodiment shown in FIGS. 19-27 includes a one-piece piston rod.

Figure 19:
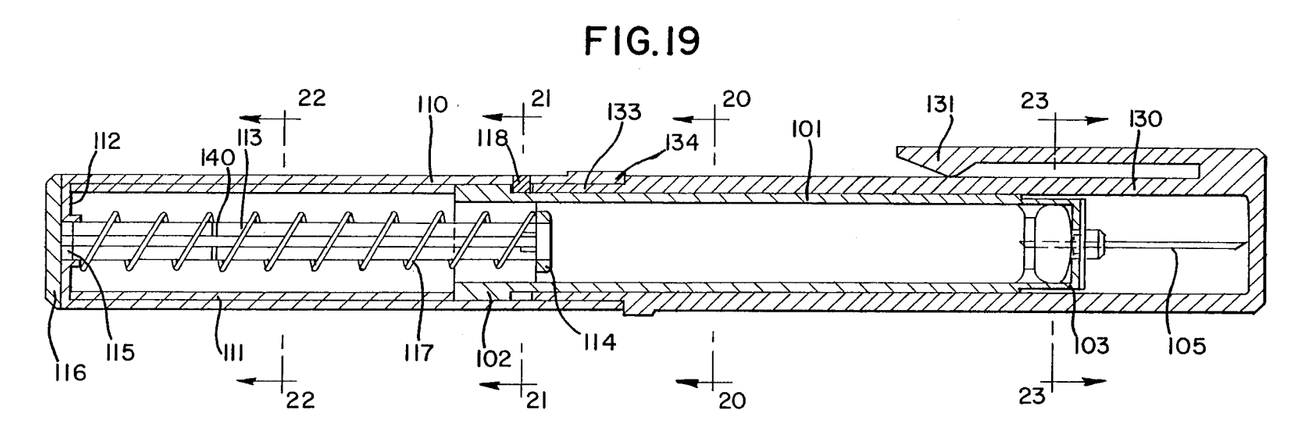
FIG. 19 is a longitudinal sectional view of a third embodiment of a dosage unit according to this invention.
Figure 20:
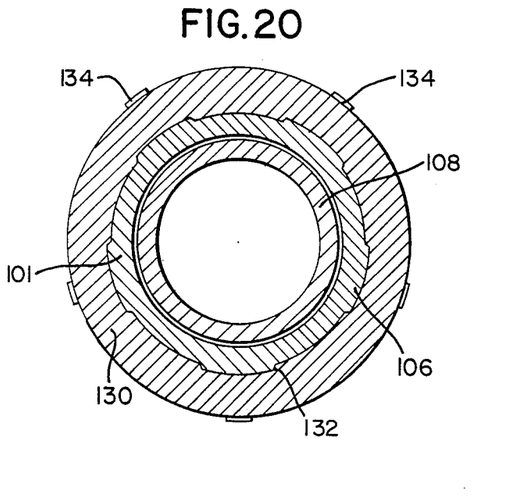
FIG. 20 is a cross-sectional view taken along the line 20—20 of FIG. 19.
Figure 21:
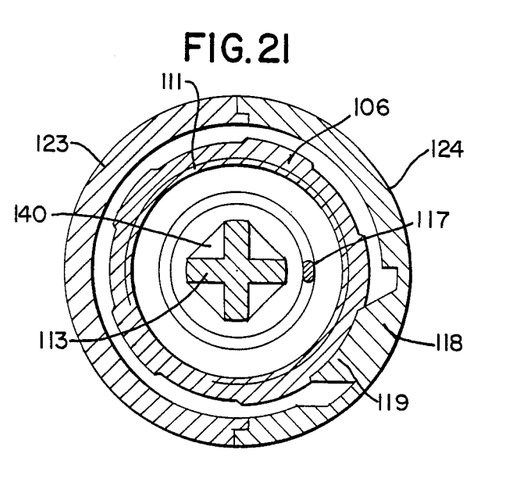
FIG. 21 is a cross-sectional view taken along the line 21—21 of FIG. 19.
Figure 22:
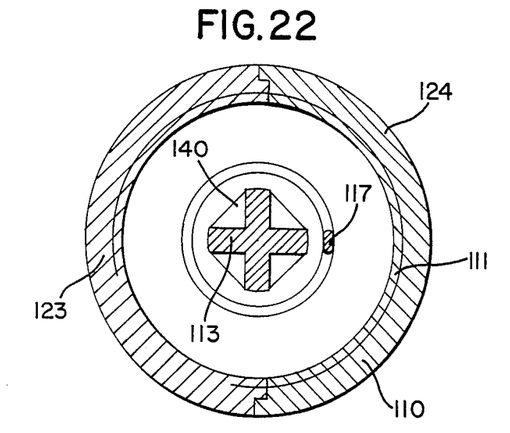
FIG. 22 is a cross-sectional view taken along the line 22—22 of FIG. 19.
Figure 23:
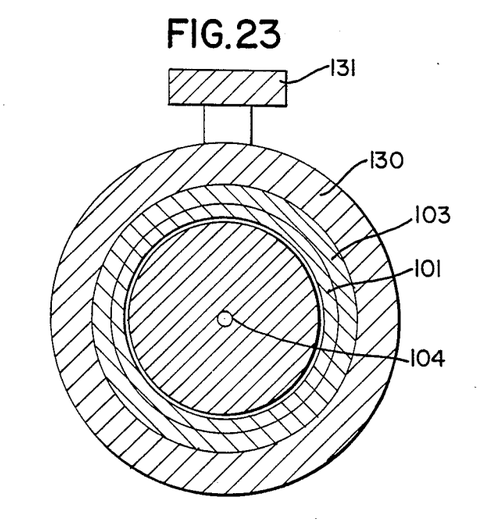
FIG. 23 is a cross-sectional view taken along the line 23—23 of FIG. 19.

The disposable syringe illustrated in FIGS. 19-27 comprises a first housing element 101 shaped to receive a liquid filled cartridge (see FIGS. 20, 23). The liquid filled cartridge is preferably of a conventional type and comprises at its front end a rubber membrane, which can be pierced by a needle, and at its rear end an axially displaceable piston. The rear end of the first housing element 101 comprises a relatively short external thread 102 capable of cooperating with an internal thread in a second housing element described below.

A needle assembly, comprising a hub 103, a double pointed needle 104 and internal threads 105, is screwed onto the front end of the first housing element 101. This causes the rear end of the needle 104 to penetrate the rubber membrane of the liquid filled cartridge when the latter is pressed into position against the front end of the first housing element 101.

The first housing element 101 is preferably made of a transparent plastic material, and it comprises five equally spaced longitudinally extending ribs 106 (see FIGS. 20 and 21). The disposable syringe further includes a second housing element 110 surrounding at least the rear end of the first housing element 101 and having an internal thread 111 that cooperates with the external thread 102 on the first housing element 101. The mating threads on the first and second housing elements 101, 110 are configured such that clockwise rotation of the first housing element 101 with respect to the second housing element 110 causes the first housing element 101 to be axially displaced towards the rear end of the second housing element 110. The second housing element 110 includes a rear end wall 112, and the syringe further includes a central, axially displaceable piston rod 113. The front end of the piston rod 113 comprises a collar 114, and the rear end of the piston rod 113 extends through an opening 115 in the end wall 112 and terminates in a pressure receiving element 116. A coil spring 117 surrounds the piston rod 113 and is tensioned between the collar 114 and the interior side of the end wall 112. This coil spring 117 tends to press the front end of the piston rod 113 against the piston of the cartridge located within the first housing element 101, and to maintain the pressure receiving element 116 in contact with the exterior of the end wall 112.

The second housing element 110 also comprises a combined pawl and click mechanism 118. This mechanism 118 extends into the interior of the second housing element 110 and includes a projection 119 having the shape of a saw tooth in contact with the exterior surface of the first housing element 101 and in particular the ribs 106 in such a manner that a counterclockwise rotation of the first housing element 101 relative to the second housing element 110 requires a predetermined force which is greater than the force required to cause clockwise rotation. The mechanism 118 is resiliently connected with the second housing element 110 in such a manner that a click is produced when the projection 119 slides over a rib 106 on the exterior of the first housing element 101.

The second housing element 110 includes at its front end an axially extending recess 120, which cooperates with an axially extending rib provided on a protecting cap described below. The second housing element 110 also defines two axially spaced annular grooves 121, 122 which are positioned on the interior side of the second housing element 110 near the front end. The grooves 121, 122 cooperate with an annular locking ring provided on the protecting cap described below.

As shown in FIGS. 21 and 22, the second housing element 110 is composed of two parts 123, 124 which are interconnected with one another at a plane that extends axially of the second housing element 110.

The disposable syringe further includes a protecting cap 130 which carries at its front end a clip 131. The protecting cap 130 defines at an internal surface five axially extending grooves 132, shaped to receive the ribs 106 provided on the exterior surface of the first housing element 101. The mating ribs 106 and grooves 132 form splines that rotationally engage the protecting cap 130 with the first housing element 101. For this reason, when the protecting cap 130 is positioned over the first housing element 101, rotation of the protecting cap 130 automatically causes a similar rotation of the first housing element 101.

The rear end of the protecting cap 130 includes a section 133 of a reduced diameter sized to fit within the front end of the second housing element 110. At the rear end of the portion of the protecting cap 130 having the full diameter of the protecting cap 130, there are provided a number of axially extending ribs 134, and one of these ribs 135 is shaped as a projection which extends into the section 133 of reduced diameter. The projecting rib 135 is shaped to be inserted into the recess 120 so as to prevent relative rotation between the protecting cap 130 and the second housing element 110.

Figure 26:
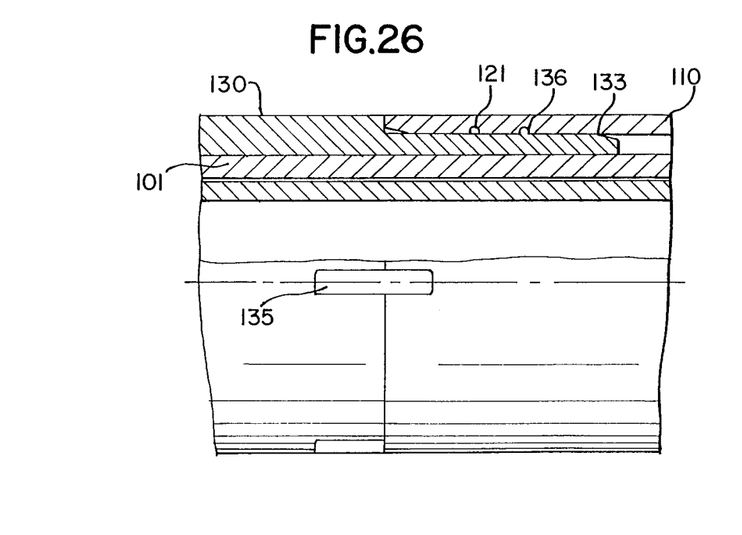
FIG. 26 is a partial longitudinal sectional view of the syringe of FIG. 19, showing the cap fully inserted into the second housing element.
Figure 27:
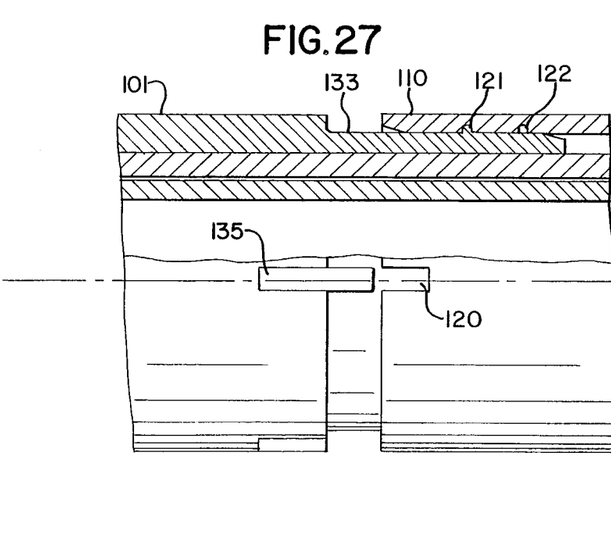
FIG. 27 is a view corresponding to FIG. 26 showing the cap partially removed from the second housing element.

The reduced diameter section 133 defines an external annular locking ring 136 that is shaped to fit into either one of the grooves 121 or 122 on the interior surface of the second housing element 110 (FIGS. 26 and 27).

When delivered to the patient the syringe of FIGS. 19 through 27 is loaded with a liquid filled cartridge, and the protecting cap 130 is inserted in the second housing element 110 with the projecting rib 135 on the protecting cap 130 inserted into the recess 120 in the second housing element 110. In this position, the annular rib 136 is located in the groove 122 (FIG. 26) and the protecting cap 130 is prevented from rotating relative to the second housing element 110.

Figures 24, 25:
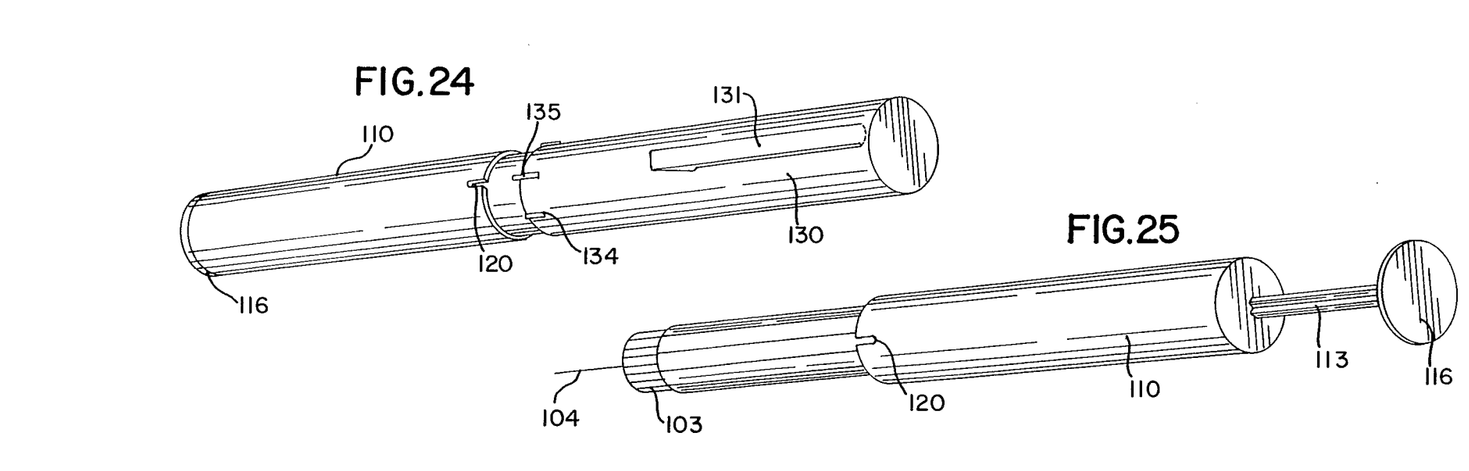
FIG. 24 is a perspective view of the syringe of FIG. 19, showing the cap partially removed.
FIG. 25 is a perspective view of the syringe of FIG. 19, showing the cap fully removed.

Before setting the dose to be injected, the patient must axially displace the protecting cap 130 relative to the first housing element 101, preferably to a position in which the annular rib 36 is located in the groove 121 (FIG. 27). At this point, the patient is free to rotate the protecting cap 130 and the first housing element 101 to set the dose. By using the recess 120 as the zero point, the patient can select a desired dose by rotating the protecting cap 130 over an angle corresponding to a given number of the ribs 134 on the exterior surface of the protecting cap 130. Rotation of the first housing element 101 will cause the piston rod 113 to be axially displaced towards the rear end of the second housing element 110, thus axially displacing the pressure receiving element 116 from the exterior side of the end wall 112. After the desired dosage has been selected, the protecting cap 130 is removed and the syringe is now prepared for an injection (FIG. 25).

The injection is effected by depressing the pressure receiving element 116. Such a depression will cause the piston of the cartridge to be axially moved towards the front end of the syringe, thereby delivering the desired preset dosage of liquid from the tip of the needle 104. After the injection has been completed, the protecting cap 130 is reinserted on the end of the housing 101 with the rib 135 located in the recess 120, and the syringe is again ready for presetting an injection of another preset dosage of liquid.

The piston rod 113 defines stop members 140 which cooperate with the interior surface of the end wall 112 if the piston rod 113 is axially displaced over a distance which is longer than acceptable. In this way, the stop members prevent the selection of a dosage that exceeds a predetermined value.

All three embodiments described above are adapted for use with a liquid filled cartridge. This is convenient for many applications, because the material for the first housing element can be chosen without concern for possible adverse reaction with the solution to be injected. However, for some applications, it may be preferable to eliminate the cartridge and use the first housing element with a suitable piston to contain the solution directly.

We claim:

1. In a disposable syringe for injecting a number of measured doses of a liquid, of the type comprising first and second housing elements coupled together to allow rotation of the first housing element with respect to the second housing element, said first housing element adapted to receive a quantity of liquid and comprising means for mounting a liquid outlet needle at a front end thereof, said second housing element having a rear end situated opposite the front end of the first housing element, the improvement comprising:
   a piston rod disposed in the second housing element to move axially therein, said piston rod comprising a rod element and a nut element, said rod element coupled to the first housing element to move axially therein without relative rotation therewith, said nut element threaded to the rod element for telescoping movement therewith and configured to move axially in the second housing element without relative rotation therein; and
   a pressure receiving element on the nut element;
   said housing, rod, nut and pressure receiving elements cooperating such that relative rotation between the housing elements in a selected direction causes relative rotation between the rod and nut elements and thereby increases the effective length of the piston rod and causes the pressure receiving element to extend from the second housing element such that a measured quantity of liquid is expressed from the needle when the pressure receiving element is moved back toward the second housing element.

2. The invention of claim 1 wherein the first and second housing elements are coupled together for rotation without axial displacement therebetween.

3. The invention of claim 1 wherein the pressure receiving element defines a first stop surface that limits travel of the nut element inwardly, towards the first housing element.

4. The invention of claim 2 wherein the nut element defines an axially oriented scale positioned to indicate the axial position of the nut element with respect to the second housing element.

5. The invention of claim 4 wherein the scale is integrally formed on the nut element.

6. The invention of claim 1 wherein the first housing element is configured to receive a cartridge having a pierceable diaphragm at a front end thereof, a slideable piston at a rear end thereof, and containing the quantity of liquid.

7. The invention of claim 2 wherein the nut element defines at least one radially protruding, axially extending projection on an exterior portion thereof, and wherein the projection is received in an axially extending groove in an inner portion of the second housing element.

8. The invention of claim 1 wherein the nut element comprises a second stop surface configured to contact the second housing element to limit axial movement of the nut element out of the second housing element.

9. The invention of claim 1 wherein the nut element and the pressure receiving element are substantially axially symmetrically shaped, and wherein the pressure receiving element defines an outer diameter substantially equal to that of the second housing element.

10. The invention of claim 1 further comprising
    a removable protective cap configured to receive the first housing element and substantially abut the second housing element while mounted on the first housing element; and
    means for releasably coupling the protective cap and the first housing element for rotation together such that rotation of the protective cap with respect to the second housing element causes rotation of the first housing element with respect to the second housing element.

11. The invention of claim 10 wherein the substantially abutting front portion of the second housing element and rear portion of the protective cap together comprise scale means for measuring relative rotation of the protective cap with respect to the second housing element.

12. The invention of claim 11 further comprising means for providing detents at selected rotational positions of the first housing element with respect to the second housing element.

13. The invention of claim 12 wherein the coupling means allows the protective cap to receive the first housing element in multiple different angular positions of the protective cap with respect to the first housing element to allow the protective cap to be oriented at a selected position with respect to the second housing element, regardless of the detent rotational position of the first housing element in the second housing element.

14. The invention of claim 10 wherein the substantially abutting front portion of the second housing element and rear portion of the protective cap together comprise interlocking means for defining a selected angular position of the protective cap with respect to the second housing element.

15. The invention of claim 14 wherein the interlocking means comprises a recess on the rear portion of the protective cap and a projection on the front portion of the second housing element, said projection shaped to fit into the recess to define the selected angular position.

16. The invention of claim 1 wherein the rod element defines at least one toothed axial groove, and wherein the rod element is coupled to the first housing element by at least one pawl that rides in the groove to prevent rotation of the rod element in the first housing element, said pawl engaging the toothed groove to prevent retraction of the rod element.

17. The invention of claim 16 wherein the at least one groove in the rod element comprises two diametrically opposed grooves, and wherein the at least one pawl comprises two pawls, one riding in each of the grooves.

18. The invention of claim 16 wherein the liquid is contained in a cartridge and wherein the first housing element comprises a locking ring that snaps in place to lock the cartridge within the first housing element.

19. The invention of claim 18 wherein the locking ring mechanically interlocks with a mating portion of the first housing element to prevent rotation therebetween.

20. In a disposable syringe for injecting a number of measured doses of a liquid, of the type comprising first and second housing elements coupled together to allow rotation of the first housing element with respect to the second housing element, said first housing element adapted to receive a quantity of liquid and comprising means for mounting a liquid outlet needle at a front end thereof, said second housing element having a rear end situated opposite the front end of the first housing element, the improvement comprising:

a piston rod disposed in the second housing element to move axially therein, said piston rod comprising a piston actuating end and a force receiving end, said force receiving end positioned at the rear end of the second housing element when in an initial position;

means, responsive to relative rotation between the first and second housing elements, for causing the force receiving end of the piston rod to move away from the initial position to preset a dose to be delivered through the needle when the force receiving end is returned to the initial position;

a protective cap removably mounted over the front end of the first housing element to protect the needle; and means for releasably coupling the protective cap and the first housing element for rotation together such that rotation of the protective cap with respect to the second housing element causes rotation of the first housing element with respect to the second housing element.

21. The invention of claim 20 wherein the protective cap is configured to receive the first housing element such that a front portion of the second housing element substantially abuts a rear portion of the protective cap when the protective cap is mounted in place over the first housing element.

22. The invention of claim 21 wherein the substantially abutting front portion of the second housing element and rear portion of the protective cap together comprise scale means for measuring relative rotation of the protective cap with respect to the second housing element.

23. The invention of claim 22 wherein the scale means comprises a circumferential scale on the rear portion of the protective cap and a marker on the front portion of the second housing element.

24. The invention of claim 20 wherein the releasably coupling means comprises a set of interengaging splines on the protective cap and the first housing element.

25. The invention of claim 24 wherein the splines are configured to allow the protective cap to receive the first housing element in multiple different angular positions of the protective cap with respect to the first housing element.

26. The invention of claim 21 wherein the substantially abutting front portion of the second housing element and rear portion of the protective cap together comprise interlocking means for defining a selected angular position of the protective cap with respect to the second housing element.

27. The invention of claim 26 wherein the interlocking means comprises a recess on the rear portion of the protective cap and a projection on the front portion of the second housing element, said projection shaped to fit into the recess to define the selected angular position.

28. The invention of claim 20 wherein the piston rod comprises a rod element and a nut element threadedly engaged with the rod element, and wherein the nut element is configured to move axially without rotating in the second housing element.

29. The invention of claim 28 further comprising ratchet means for preventing the rod element from retracting from the first housing element while allowing the rod element to move into the first housing element.

30. The invention of claim 20 wherein the first housing element is configured to receive a cartridge having a pierceable diaphragm at a front end thereof, a slideable piston at a rear end thereof, and containing the quantity of liquid.

* * * * *